(12) United States Patent
Lee et al.

(10) Patent No.: US 9,123,095 B2
(45) Date of Patent: Sep. 1, 2015

(54) METHOD FOR INCREASING THE ROBUSTNESS OF COMPUTER-AIDED DIAGNOSIS TO IMAGE PROCESSING UNCERTAINTIES

(75) Inventors: Michael Chun-chieh Lee, Bronx, NY (US); Lilla Boroczky, Mount Kisco, NY (US)

(73) Assignee: Koninklijke Philips N.V., Eindhoven (NL)

( * ) Notice: Subject to any disclaimer, the term of this patent is extended or adjusted under 35 U.S.C. 154(b) by 724 days.

(21) Appl. No.: 13/061,966

(22) PCT Filed: Sep. 9, 2009

(86) PCT No.: PCT/IB2009/053952
§ 371 (c)(1),
(2), (4) Date: Mar. 3, 2011

(87) PCT Pub. No.: WO2010/035163
PCT Pub. Date: Apr. 1, 2010

(65) Prior Publication Data
US 2011/0172514 A1    Jul. 14, 2011

Related U.S. Application Data

(60) Provisional application No. 61/100,864, filed on Sep. 29, 2008.

(51) Int. Cl.
*G06K 9/00* (2006.01)
*G06T 7/00* (2006.01)
(Continued)

(52) U.S. Cl.
CPC ............ *G06T 7/0012* (2013.01); *G06F 19/345* (2013.01); *G06K 9/6262* (2013.01); *G06K 9/6292* (2013.01); *G06K 2209/051* (2013.01); *G06T 2207/10072* (2013.01);
(Continued)

(58) Field of Classification Search
USPC ............. 382/12, 131–133; 128/922; 600/300; 706/924
See application file for complete search history.

(56) References Cited

U.S. PATENT DOCUMENTS 6,996,549 B2    2/2006    Zhang et al.
7,113,636 B2    9/2006    Ii et al.
(Continued)

FOREIGN PATENT DOCUMENTS

WO    02059828 A2    8/2002
WO    2006054271 A2    5/2006

OTHER PUBLICATIONS

Christoyianni et al ("Computer aided diagnosis of breast cancer in digitized mammograms", Computerized Medical Imaging and Graphics 26 (2002)).*

(Continued)

*Primary Examiner* — Shervin Nakhjavan

(57) ABSTRACT

A classifier (20) is trained by a feature matrix (18, 18') made up of feature vectors ($F1^1, \ldots, Fk^m$). The feature vectors are generated by operating on each of a plurality (k) of training image data sets with each of a plurality (m) of image processing algorithms ($12^1, \ldots, 12^m$) to generate processed and segmented images. Features of the segmented regions are extracted (14) to generate the feature vectors. In this manner, the classifier is trained with data generated with a variety of image processing algorithms.

17 Claims, 5 Drawing Sheets

(51) Int. Cl.
*G06F 19/00* (2011.01)
*G06K 9/62* (2006.01)

(52) U.S. Cl.
CPC .............. *G06T 2207/20081* (2013.01); *G06T 2207/20084* (2013.01); *G06T 2207/30064* (2013.01)

(56) References Cited

U.S. PATENT DOCUMENTS

| | | | | |
|---|---|---|---|---|
| 7,308,126 | B2 * | 12/2007 | Rogers et al. | 382/132 |
| 7,515,743 | B2 * | 4/2009 | Kiraly et al. | 382/131 |
| 7,711,174 | B2 * | 5/2010 | Sammak et al. | 382/133 |
| 7,949,181 | B2 * | 5/2011 | Padfield et al. | 382/164 |
| 8,073,253 | B2 * | 12/2011 | Li et al. | 382/173 |
| 8,131,039 | B2 * | 3/2012 | Krishnapuram et al. | 382/128 |
| 8,170,330 | B2 * | 5/2012 | Kiraly et al. | 382/159 |
| 8,265,355 | B2 * | 9/2012 | Zhao et al. | 382/128 |
| 8,340,437 | B2 * | 12/2012 | Abramoff et al. | 382/224 |
| 8,345,940 | B2 * | 1/2013 | Mattiuzzi et al. | 382/128 |
| 8,346,483 | B2 * | 1/2013 | Kil | 702/19 |
| 8,798,374 | B2 * | 8/2014 | Bartlett et al. | 382/197 |
| 2003/0120134 | A1 * | 6/2003 | Rao et al. | 600/300 |
| 2006/0018524 | A1 * | 1/2006 | Suzuki et al. | 382/128 |
| 2006/0064017 | A1 * | 3/2006 | Krishnan et al. | 600/450 |
| 2006/0111644 | A1 * | 5/2006 | Guttag et al. | 600/544 |
| 2006/0184475 | A1 * | 8/2006 | Krishnan et al. | 706/20 |
| 2006/0210133 | A1 * | 9/2006 | Krishnan et al. | 382/128 |
| 2007/0055153 | A1 * | 3/2007 | Simopoulos et al. | 600/437 |
| 2007/0081712 | A1 * | 4/2007 | Huang et al. | 382/128 |
| 2007/0110292 | A1 * | 5/2007 | Bi et al. | 382/128 |
| 2007/0154099 | A1 * | 7/2007 | He et al. | 382/224 |
| 2007/0189602 | A1 * | 8/2007 | Rao et al. | 382/159 |
| 2008/0125643 | A1 * | 5/2008 | Huisman et al. | 600/420 |
| 2008/0159613 | A1 * | 7/2008 | Luo et al. | 382/132 |
| 2008/0201280 | A1 * | 8/2008 | Martin et al. | 706/12 |
| 2009/0028403 | A1 * | 1/2009 | Bar-Aviv et al. | 382/128 |
| 2009/0161928 | A1 * | 6/2009 | Khamene et al. | 382/128 |
| 2009/0204557 | A1 * | 8/2009 | Zhang | 706/12 |
| 2012/0219200 | A1 * | 8/2012 | Reeves et al. | 382/131 |

OTHER PUBLICATIONS

Dietterich, T. G.; Ensemble Methods in Machine Learning; "Multiple Classifier Systems, Book Series Lecture Notes in Computer Science"; 2000; Abstract.

Miller, M. T., et al.; Feature Selection for Computer-Aided Polyp Detection using Genetic Algorithms; 2003; Proc. SPIE; vol. 5031; pp. 102-110.

Mohamed, S. S.; Integrated Feature Analysis for Prostate Tissue Characterization Using TRUS Images; 2006; Thesis to University of Waterloo, Ontario, Canada.

* cited by examiner training data matrix 18

$$\begin{vmatrix} F_1^1 \\ F_1^2 \\ \vdots \\ F_1^m \\ F_2^1 \\ F_2^2 \\ \vdots \\ F_2^m \\ F_k^1 \\ F_k^2 \\ \vdots \\ F_k^m \end{vmatrix}$$

FIG. 2 training data matrix $18^1$ $$\begin{vmatrix} F_1^1 & F_1^2 & \cdots & F_1^m \\ F_2^1 & F_2^2 & \cdots & F_2^m \\ & & \vdots & \\ F_k^1 & F_k^2 & \cdots & F_k^m \end{vmatrix}$$

FIG. 3

Distribution of classifier performance (ROC Az)

| testing data | training data | |
|---|---|---|
| | manual [1] | all [2] |
| manual | 0.85 ± 0.03 | 0.84 ± 0.03 |
| simulated mean | 0.809 | 0.800 |
| simulated SD | 0.022 | 0.017 |
| 95th percentile | 0.844 | 0.827 |
| 75th percentile | 0.824 | 0.811 |
| 50th percentile | 0.810 | 0.800 |
| 25th percentile | 0.795 | 0.789 |
| 5th percentile | 0.773 | 0.772 |
| best-case | 0.972 | 0.938 |
| worst-case | 0.334 | 0.550 |

[1] trained on manually selected segmentation;
[2] trained on all segmentations;

METHOD FOR INCREASING THE ROBUSTNESS OF COMPUTER-AIDED DIAGNOSIS TO IMAGE PROCESSING UNCERTAINTIES

The present application relates to the art of computer-aided diagnosis (CADx). It finds particular application in conjunction with computer-aided diagnosis based on diagnostic images and will be described with particular reference thereto. However, it will be appreciated that the present application is also applicable to other computer-aided diagnostic systems which may, or may not, include images.

Computer-aided diagnosis systems have been proposed as a method to aid in the accurate characterization of abnormalities found in diagnostic medical images. For example, computer-aided diagnosis can be used to detect pulmonary nodules in CT scans. The CADx system analyses the CT images, or at least the portion associated with detected nodules, and estimates the likelihood a given nodule is malignant or benign.

Typically, initial image processing is performed to prepare the images for analysis. Looking again to the example of CADx for pulmonary nodules, an initial segmentation step is used to define the boundaries of each nodule. These boundaries then serve as the input for the CADx system. The CADx system performs a feature extraction that quantifies numerous characteristic features describing the nodule, e.g., 100 or more features. These features, for example, may include shape, texture, contrast, size, and the like. The segmented boundaries allow differential analysis of the internal and external characteristics of the nodule, as well as describing the shape and size of the nodule. A pattern classification algorithm is applied to classify an unknown nodule on the basis of this group of computed characteristic features. This classification is divided into groups, such as benign or malignant. Such classification algorithms or "classifiers", are trained using a set of training data. The training data typically includes images which have previously undergone segmentation or other image processing and feature extraction, and for which the correct classification, e.g., diagnosis, is already known.

A problem can arise due to uncertainty associated with the image processing. For example, consider a simple classifier which assesses the diagnosis of a pulmonary nodule by its volume and contrast, i.e., a mean brightness of the inside of the nodule divided by a mean brightness of its surroundings. If two segmentation algorithms are used for preprocessing and produce two different borders, these borders are likely to lead to different volumes, i.e., the volume or area contained within the border, as well as different contrast values. Nodule segmentation is subjective. That is, there is no absolute definite answer as to what the correct border is. Rather, it is possible that two different segmentation routines can derive different borders, both of which are reasonable. The question then arises as to which segmentation to use for creating the training data set and for performing the actual computer-aided diagnosis task.

In some training procedures, the features to be used in the classification are selected first. Using too many features in the classification algorithm can be problematic, particularly if irrelevant features are included. Excess features can lead to over-fitting, in which noise or irrelevant features may exert undue influence on the classification decisions because of the finite size of the training data. The process of choosing an ideal subset of features is known as "feature selection". Feature selection may be affected by uncertainties in the image processing step. Some features may be more subject to the uncertainty than others. For example, the surface area of the segmentation boundary may be more sensitive than the overall volume, particularly because many segmentation algorithms are designed to produce consistent volume measurements but may, consequently, yield locally different shapes.

Other types of image processing besides segmentation are typically performed. However, segmentation is a particularly acute challenge in the development of a clinically viable CADx system. Other image processing steps may contain an element of uncertainty that affects CADx results. For example, interpolation using different kernels may each produce visually acceptable results, but which each lead to a different set of features, and hence potentially different classifications. Registration is used to align multiple images of the same patient or align a single patient with a reference atlas. Different registration algorithms are again likely to produce visually similar results, but may yield different computational features and different classifications. Similar uncertainty effects may be observed due to filtering or de-noising of images, image enhancement such as image sharpening, or reconstruction algorithms.

Various segmentation techniques have been employed such as distance transformations and region growing. In an exemplary segmentation technique for lung nodules, the segmentation process is initialized with a thresholding step. The initial threshold is critical in determining the final shape of the segmented nodule. A threshold of −400 Hounsfield units (HU) has been found to represent a reasonable value that yields relatively consistent nodule volume estimates over a range of slice thicknesses for several segmentation algorithms. However, some nodules are not satisfactorily segmented using this threshold and are instead segmented with a different threshold.

To overcome this challenge for both training and testing, the segmentation threshold can be varied manually for each nodule until a visually acceptable segmentation is obtained. While this approach has met considerable success, the issue of user subjectivity still introduces uncertainty. The manual selection of segmentations by a variety of clinicians leads to difficulties in maintaining consistency when diagnosing images. The effect of user subjectivity tends to result in segmentation with a high variability across different radiologists. This subjectivity is exacerbated if the user is allowed to modify the segmentation result through the use of computer editing tools.

A key challenge to CADx systems is robustness in the face of the uncertainties associated with the image processing step. "Robust" connotes that the precision and accuracy of CADx output diagnosis using any reasonable image processing routine will remain relatively the same despite uncertainties. Problems to be overcome include training a classifier that is resilient to the uncertainties in the image processing steps and selecting features that are resilient to the uncertainties in the image processing steps.

A proposed attempt to address the above-identified problems is to simply specify a single image processing algorithm and parameters for that algorithm to be used in all diagnostic cases. In the lung nodule CADx example, this typically involves specifying a segmentation routine and a single fixed threshold. However, as described above, it is not always possible to find common algorithms, thresholds, or features that are applicable in all cases.

Others have proposed removing the image processing step altogether, and performing the analysis and classification based on the raw image data without extracting features. Although such a proposal has been relatively successful, in many instances segmentation of the nodule is still desirable.

For example, volume measurements are typically performed on nodules in order to track progression or treatment efficacy. Additionally, analyzing the raw data does not aid in other image processing algorithms, such as registration, filtering, and interpolation.

Others have proposed improving generalization performance of CADx systems by adding noise to the data before using the data in a training routine. This is typically done by creating multiple replicas of each training data point, but each time adding a different level of random noise to the position of that data point. One drawback is the difficulty in matching the artificial noise to the actual uncertainty associated with the image processing algorithms.

The present application contemplates a new and improved training technique which overcomes the above-referenced problems and others.

In accordance with one aspect, a classifier is provided. The classifier includes at least one of a linear discriminant processor, a support vector machine, a neural network, a Bayesian processor, a decision tree, or a nearest neighbor processor which has been taught by a feature matrix made up of feature vectors. Each of the feature vectors of the feature matrix is generated by processing diagnostic image data with each of a plurality of image processing algorithms and one or more feature extraction algorithms.

In accordance with another aspect, a method is provided for training a classifier for use in computer-aided diagnosis (CADx). Training image data sets from each of a plurality of patients with known diagnoses are processed with each of a plurality of image processing algorithms to generate a plurality of processed and segmented training images. Features of the processed and segmented images are extracted. The classifier is trained with the extracted features and the known diagnosis.

In accordance with another aspect, a method of training a classifier for a computer-aided diagnostic system is provided. A plurality of training image data sets is generated from a plurality of patients with known diagnoses. Each of the image data sets is processed with each of a plurality of image processing algorithms to generate processed and segmented training images. Features of the processed and segmented images are extracted to generate feature vectors. The classifier is trained with the generated feature vectors to recognize the known diagnosis.

One advantage resides in a more robust classifier.

Another advantage resides in more meaningful computer-aided diagnoses over a range of image processing techniques.

Another advantage resides in individual radiologists being able to select preferred image processing techniques without adversely affecting computer-aided diagnosis.

Another advantage resides in software developers being able to create new versions of the computer-aided diagnosis software using different image processing techniques without adversely affecting computer aided diagnosis.

Still further advantages and benefits will become apparent to those of ordinary skill in the art upon reading and understanding the following detailed description.

The invention may take form in various components and arrangements of components, and in various steps and arrangements of steps. The drawings are only for purposes of illustrating the preferred embodiments and are not to be construed as limiting the invention.

FIG. 2 illustrates one example of a training data matrix;

FIG. 3 illustrates a second embodiment of a training data matrix;

Figure 6C:
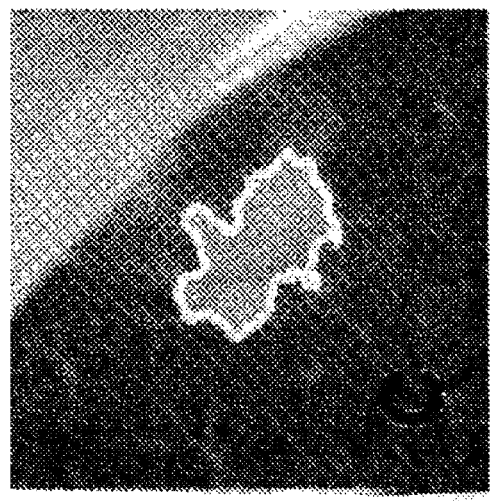
Figure 6B:
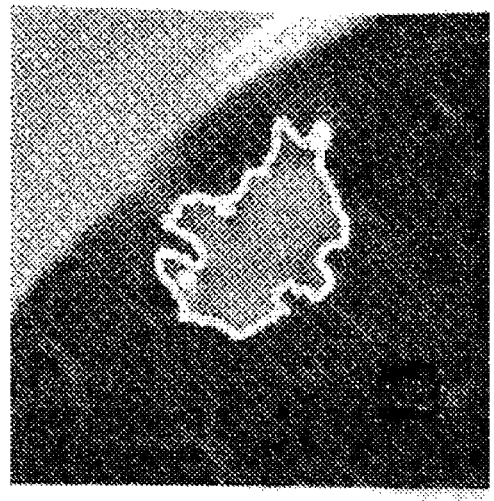
Figure 6A:
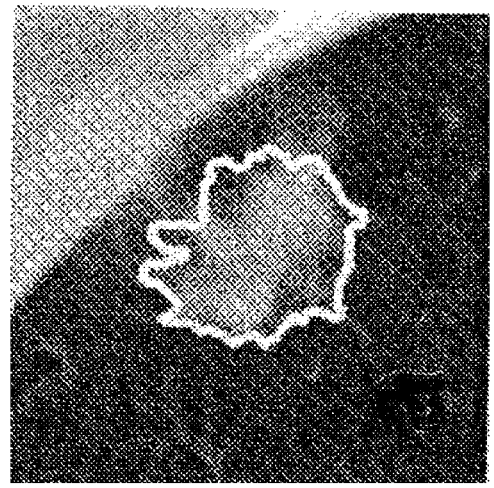
Figures 7, 8:
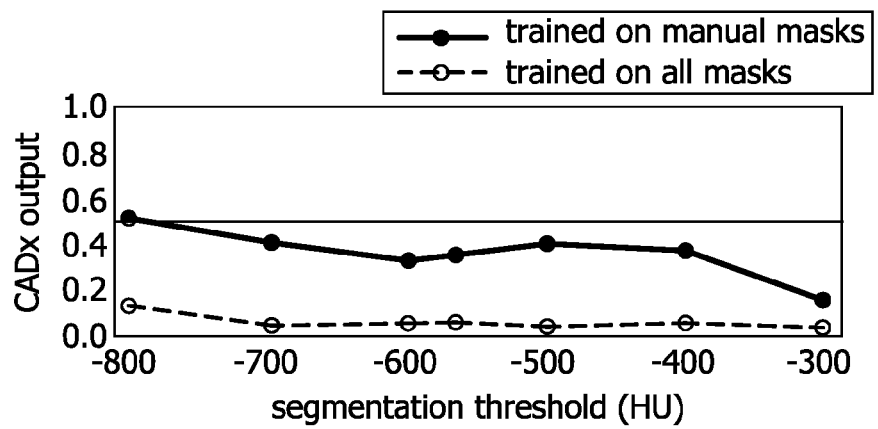

FIGS. 6a, 6b, and 6c illustrate variations in segmentation results using different thresholds;

FIG. 7 is a graphic illustration of CADx probabilities of malignancy across segmentation thresholds for a benign nodule; and FIG. 8 is a table illustrating distribution of classifier performance.

The present application is related to a robust classifier and a method for training a classifier to be robust to the uncertainties associated with image or other processing steps. The present classifier is trained by the repeated application of different image processing algorithms and feature extractions to the training data such that the resulting features capture the uncertainty of the range of image processing algorithms. The present application also relates to the classifier constructed based on this enlarged training data set.

Figure 1:
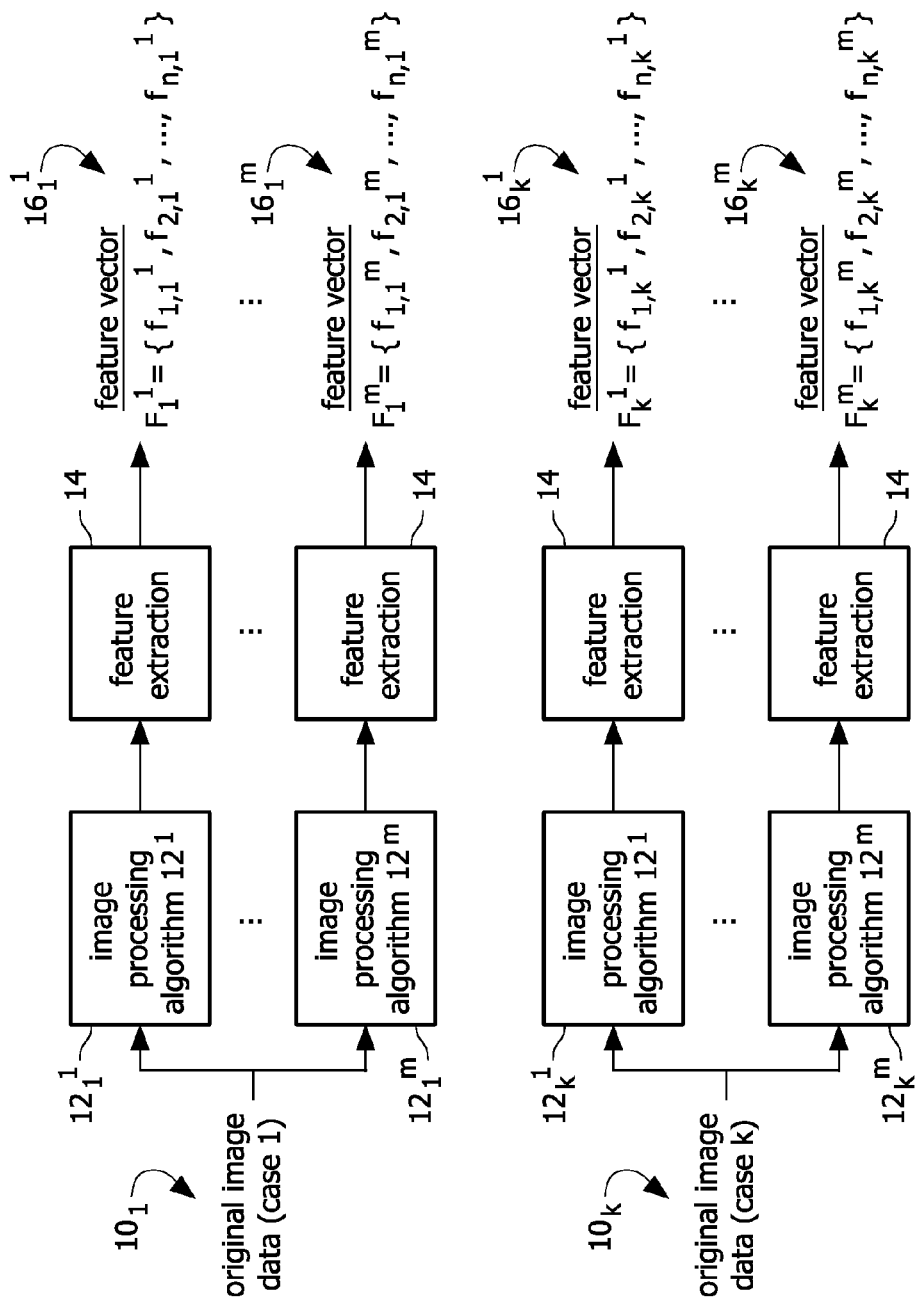
FIG. 1 is a schematic diagram of a training data preparation process.

With reference to FIG. 1, original or raw image data $10_1$ is operated upon with an image processing step $12_1^{\ 1}$ which uses a first image processing algorithm $12^1$. Once the image is processed, the image is subject to a feature extraction step 14 to extract the features which are assembled to create a feature vector output $16_1^{\ 1}$ with a feature vector $F_1^{\ 1}$. The process is repeated m times to subject the original image data $10_1$ to an image processing step $12_1^{\ 1}, \ldots, 12_1^{\ m}$ for each of the m image processing algorithms $12^1, \ldots, 12^m$. Each of the processed images are subject to the feature extraction step 14 to generate a corresponding feature vector output $16_1^{\ 1}, \ldots, 16_1^{\ m}$. In this manner, m feature vectors $F_1^{\ 1}, \ldots, F_1^{\ m}$, are generated from the original image data $10_1$.

This operation is repeated for each of k original image data sets $10_1, \ldots, 10_k$, where k is a plural value, in some embodiments greater than 100. Each of the k original image data sets is thus subject to the image processing steps $12_1^{\ 1}, \ldots, 12_k^{\ 1}$ in which the image is processed first by using the first image processing algorithm $12^1$. The processed images are each subject to the feature extraction step 14 to generate the feature vector outputs $16_1^{\ 1}, \ldots, 16_k^{\ 1}$ of the feature extraction vector $F_1^{\ 1}, \ldots, F_k^{\ 1}$. Each of the k original image data sets is similarly subject to the m image processing steps $12_1^{\ 1}, \ldots, 12_k^{\ m}$, and hence each of the m image processing algorithms; that is, a total of m×k image processing operations. Each of the processed images is subject to the feature extraction step 14 to generate a feature vector output $16_1^{\ 1}, \ldots, 16_k^{\ m}$ depicting one of the feature vectors $F_1^{\ 1}, \ldots, F_k^{\ m}$. The image processing includes different segmentation methods, different interpolation methods, different registration algorithms, different filters, and the like. Each image data set and image processing algorithm creates a different processed image which is then subject to the feature extraction. In this manner, a single input image generates m feature vectors and k input images generate m×k feature vectors. It is to be appreciated that the above-described steps can be implemented on a single computer or processor, or by a plurality of processors, ASICs, or other means.

As illustrated in FIG. 2, the feature vectors are assembled into a training data matrix 18, with m×k rows and n columns, where n is the number of features extracted. As shown in FIG. 3, an alternate training data matrix 18' has k rows with m×n columns, representing different features extracted with different processing algorithms. As used herein, matrix is to be constructed as including tensors and other multi-linear functions.

The training data sets and the processed images are used in feature selection and training for classifiers or classifier ensembles. More specifically, feature selection or classifier training is performed using the training data matrix of FIG. 2 or 3. This effectively enlarges the number of training points used in the training algorithm or increases the dimensionality of the training space. A classifier ensemble is constructed by performing feature selection and/or classifier training on the training data matrices shown in FIG. 2 or 3. The classifiers include one or more of a linear discriminant, a support vector machine, a neural network, a Bayesian classifier, a decision tree, a nearest neighbor classifier, or the like. Feature selection includes a combination of genetic algorithms, stepwise searches, exhaustive searches, principal component analysis, discriminant analysis, and the like. It is to be appreciated that the above-described steps can be implemented on a single computer or processor, or by a plurality of processors, ASICs, or other means.

Figure 4:
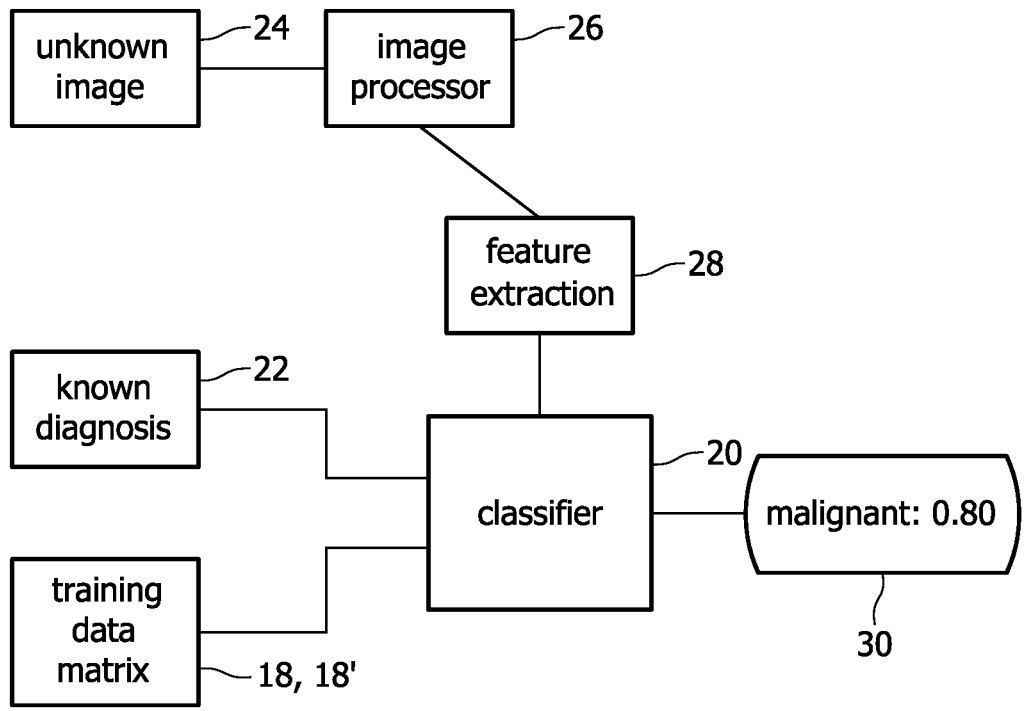
FIG. 4 is a diagrammatic illustration of a classifier in a CADx system.

More specifically, as shown in FIG. 4, a classifier 20 is trained by supplying it with the training data matrix 18 or 18' and an a priori known diagnosis 22. The classifier uses the linear discriminant, support vector machine, neural network, Bayesian classifier, decision tree, nearest neighbor classifier, or the like to determine patterns in the training data from the training data matrix 18 or 18' which correspond to the known diagnoses 22. Once the classifier has been trained, typically at a laboratory site, it is installed as part of a CADx system. Thereafter, unknown image data 24 is processed with an image processor 26 in an image processing step, which may or may not use image processing algorithms 1, . . . , m. A feature extraction processor or means 28 extracts a feature vector F in a feature extraction step, which may or may not include the same n features as were extracted by the feature extraction step 14. After analyzing the feature vector based on the patterns learned during training, the classifier 20 generates an output 30 indicative of a proposed diagnosis and a likelihood of the diagnosis being correct. In a case where a lung nodule is evaluated, the display may indicate that the nodule is malignant, with a 0.80 or 80% probability or certainty. Other information such as one or more of the features may also be displayed. Similarly, images of each nodule with or without its border as marked by the segmentation portion of the image processing algorithm may also be displayed.

In one example applied to a CADx of pulmonary nodules, the overall goal is to aid physicians reading CT or other diagnostic images by providing a second opinion as to whether a lung nodule is malignant or benign. In this example, the original image data set includes original image data for each of 125 pulmonary nodules, i.e., k=125. During the image processing step conducted by image processor 26, the data set is segmented using manually identified seed points and 6 different segmentation thresholds, i.e., m=6. Suitable segmentation thresholds include a contrast of −800 HU, −700 HU, . . . , −300 HU. Features extracted from these segmentations yield data sets $T_{-800}, T_{-700}, \ldots, T_{-300}$. Manual selection of the "best" segmentation for each nodule is performed by a researcher familiar with the feature extraction algorithm yielding a first or manual training data set $T_{manual}$. The result of all 6 thresholds is combined with the manual training data set to yield an enlarged training set $T_{all}$. This training matrix $T_{all}$ is constructed in the manner of data matrix 18 of FIG. 2, with a number of rows equal to k×m and a number of columns equal to n=215. In this example, the matrices $T_{-800}, T_{-700}, \ldots, T_{-300}, T_{manual}$ include k=125 rows and n=215 columns.

The diagnostic performance of the CADx system is tested through a leave-one-out procedure with ensembles including 500 linear discriminant classifiers. Both genetic algorithm based feature selection and classifier training are performed with each leave-one-out iteration to reduce bias. In this analysis, all points belonging to a test nodule at different segmentations are removed from training. Two sets of computational experiments are performed as follows:

1. Training on $T_{manual}$ with validation on $T_{manual}, T_{-800}, T_{-700}, \ldots, T_{-300}$; and,
2. Training on $T_{all}$ with validation on $T_{manual}, T_{-800}, T_{-700}, \ldots, T_{-300}$.

Figure 5:
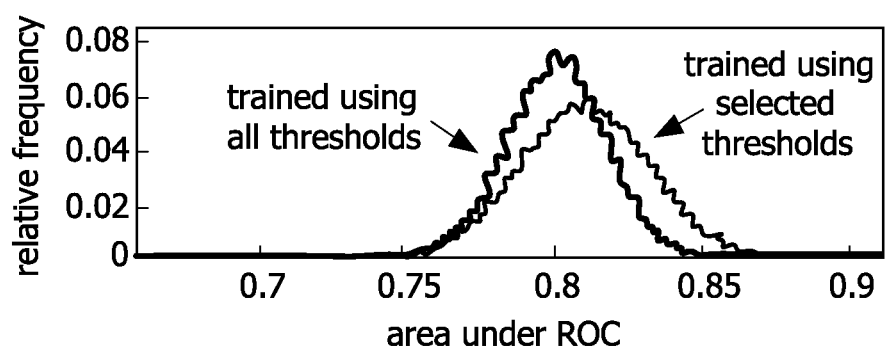
FIG. 5 illustrates relative accuracy using selected versus all thresholds.

The results are statistically analyzed. For example, consider a hypothetical user who is presented with the 6 segmentations based on thresholds −800 HU, −700 HU, . . . , −300 HU and asked to use a segmentation before proceeding with the CADx calculation. One set of simulations is performed to emulate a user who chooses the segmentation randomly. For example, a Monte Carlo approach can perform the random selection 5,000 times for each of the 125 cases. For each simulated set of segmentation choices, an area under a receiver operating characteristic (ROC) curve indicative of the accuracy is computed. See, FIG. 5. This iterative random process creates a large set of diagnosis probability values. The distribution of these values describes the performance of the CADx algorithm in the face of uncertain segmentation.

Additionally, best-case and worst-case scenarios are computed by choosing a segmentation that yields the best CADx algorithm performance, second best, and so on. For example, a malignant nodule of the best segmentation could be the one that produced the highest CADx estimate of the likelihood or probability of malignancy. Likewise, for a benign module, the best segmentation yields the lowest probability of malignancy.

An example of the impact of segmentation parameter selection is illustrated in FIG. 6a-6c. Significant discrepancies in the outline of the segmented nodule are observed for different threshold settings, despite using the same image data. FIG. 6a illustrates segmentation results for a −800 HU threshold; FIG. 6b illustrates segmentation results for a −600 HU threshold; and FIG. 6c illustrates segmentation results for a −400 HU threshold. Different users, when asked to choose the "best" segmentation, are apt to pick different ones of FIGS. 6a-6c. Similarly, if manually segmented, the manually drawn contours are likely to differ from the contours shown in FIGS. 6a-6c and the manual contours drawn by different radiologists are likely to differ from each other. The effect of this variation on the CADx output in this example is illustrated in FIG. 7. In this example, if the segmentation given in FIG. 6a is classified using a CADx system trained on manually selected segmentation results, then the system classifies the nodule as "malignant" with a probability of about 0.53. At all other thresholds, the system makes a benign classification. It is an object of this application to stabilize the CADx results for consistency with manual or threshold segmentation.

For each of the 125 cases, the range of possible CADx outputs is calculated by choosing from the segmentation threshold data set −800 HU, −700 HU, . . . , −300 HU. Each CADx output takes on values from 0 for a benign prediction to 1 for a malignant prediction. A robust classifier is expected to produce only a small range of output values when the segmentation is varied. With training on the manual segmentation data, the range of output values is observed to have a mean of 0.36 with a standard deviation of +/−0.23 across the 125 cases. For the robust system trained on matrix $T_{all}$ which contains all segmentation results formulated as in the training data matrix 18 of FIG. 2, the range was reduced to a mean of 0.27 with a standard deviation of +/−0.21 overall 125 cases. When training on manually selected data, there are only 56 cases in which the classification of malignant or benign would change based on the segmentation threshold. Using the present robust system trained on all segmentation results, there are only 41 cases in this example in which the classification is at risk of changing.

With reference to FIG. 8, a table is presented illustrating the distribution of the classifier performance. This table summarizes the variation of the CADx performance when training is performed using the different training matrices. Testing the CADx on selected manual segmentations, as in the first row, represents the performance of the CADx on data obtained based on the judgments of a single set of observers. No significant difference is observed between the two columns of the first row, indicating no difference between the conventional training method and the method described in this application.

The simulated distribution estimates the variation across a very wide spectrum of observers, each with different judgments as to which segmentation is optimal. This effect is summarized by the simulated mean, standard deviation, and percentiles, and the best-case and worst-case scenarios set forth in the table and the distributions realized in FIG. 5. Changing from the manually selected training data to training on all data results in a minor change in mean performance from 0.809 to 0.800, but reduces the standard deviation from 0.022 to 0.017, thus demonstrating the goal of increased robustness.

The described classifier and classifier training technique find application in healthcare, including image-based clinical decision support systems. Particularly, computer-aided diagnosis systems and therapy management systems which may be integrated with medical imaging systems, imaging workstations, patient monitoring systems, and healthcare informatics. Image-based computer-aided diagnosis systems include but are not limited to those for lung cancer, breast cancer, colon cancer, prostate cancer, and the like. The image data may originate from CT, MRI, ultrasound, PET, SPECT, or other imaging modalities. Integration may involve the use of radiology workstations or picture archiving and communications systems.

This disclosure refers to preferred embodiments. Modifications and alterations may occur to others upon reading and understanding the preceding detailed description. It is intended that this disclosure be construed as including all such modifications and alterations insofar as they come within the scope of the appended claims or the equivalents thereof.

The invention claimed is:

1. A system, comprising:
   memory that stores computer readable instructions;
   a processor that executes the computer readable instructions stored in the memory, which causes the processor to:
      process each of a plurality of training image data sets from a plurality of patients with known diagnoses with each of a plurality of image processing algorithms, wherein each of the training image datasets is processed with each of the plurality of image processing algorithms to produce a plurality of processed training images, and wherein each of the plurality of image processing algorithms produces one of the plurality of processed training images;
      extract features of the processed training images to generate feature vectors; and
      train a classifier with the generated feature vectors to recognize each known diagnosis of the known diagnoses.

2. The system according to claim 1, the computer readable instructions further cause the processor to:
   receive an image; and
   display a predicted diagnosis and a probability that the predicted diagnosis is correct.

3. The system according to claim 2, the computer readable instructions further cause the processor to:
   receive image data from an imager;
   process the image data to generate a processed image; and,
   extract features of the processed image.

4. The system according to claim 3, wherein the processor includes a segmentation processor.

5. The system according to claim 2, wherein the received image includes voxels representing a lung including lung nodule, and the processor generates a probability that each lung nodule is malignant.

6. A method of training a classifier for use in computer-aided diagnosis, the method comprising:
   processing each of a plurality of training image data sets from a plurality of patients with known diagnoses with each of a plurality of image processing algorithms, wherein each of the training image datasets is processed with each of the plurality of imaging processing algorithms to produce a plurality of processed training images, and wherein each of the imaging processing algorithms produces one of the plurality of processed training images;
   extracting features of the processed training images to generate feature vectors;
   training the classifier with the generated feature vectors to recognize each known diagnosis of the known diagnoses.

7. The method according to claim 6, wherein the processing step includes segmenting.

8. The method according to claim 7, wherein the segmenting includes a segmentation algorithm with a segmentation criteria including segmentation in accordance with each of a plurality of contrast thresholds.

9. The method according to claim 6, wherein a plurality of features of each processed image are extracted such that each of the feature vectors is indicative of the extracted features, for example, one or more of texture, contrast, shape, and size of the processed image or one or more subregions of the processed image.

10. The method according to claim 6, further including:
    assembling the feature vectors together into a training data matrix.

11. The method according to claim 6, further including:
    after training the classifier, supplying a diagnostic image data set with unknown diagnosis;
    image processing the unknown diagnosis data set to generate a processed unknown diagnostic image;
    extracting features from the processed unknown diagnostic image to generate an unknown diagnostic image feature vector;
    supplying the unknown diagnostic image feature vector to the classifier and generating a potential diagnosis and a probability of accuracy;
    displaying the predicted diagnosis and the probability.

12. A method of training a classifier for a computer-aided diagnostic system, the method comprising:
    generating a plurality of training image data sets from a plurality of patients, each with a known diagnosis;
    processing each training image data set with each of a plurality of image processing algorithms, wherein each of the training image datasets is processed with each of the plurality of image processing algorithms to produce a plurality of processed training images, and wherein each of the plurality of image processing algorithms produces one of the plurality of processed training images;

extracting features from the processed training images to generate feature vectors;

training the classifier with the generated feature vectors to recognize the known diagnosis.

13. The method according to claim 12, wherein the processing of the training image data set includes:

at least one of a segmentation algorithm, an interpolation algorithm, a filtering algorithm, a registration algorithm, and a reconstruction algorithm.

14. The method according to claim 12, wherein the processing includes segmenting with a segmentation algorithm with a segmentation criteria including segmentation in accordance with each of a plurality of contrast thresholds.

15. The method according to claim 12, wherein a plurality of features of each processed image are extracted such that each of the feature vectors is indicative of the extracted features, for example, one or more of texture, contrast, shape, and size of the processed image or one or more subregions of the processed image.

16. The method according to claim 12, further including:

assembling the feature vectors together into a training data matrix.

17. The method according to claim 12, further including:

after training the classifier, supplying a diagnostic image data set with unknown diagnosis;

image processing the unknown diagnosis data set to generate a processed unknown diagnostic image;

extracting features from the processed unknown diagnostic image to generate an unknown diagnostic image feature vector;

supplying the unknown diagnostic image feature vector to the classifier and generating a potential diagnosis and a probability of accuracy;

displaying the predicted diagnosis and the probability.

* * * * *